United States Patent [19]

Wheatley et al.

[11] Patent Number: 4,900,556

[45] Date of Patent: Feb. 13, 1990

[54] SYSTEM FOR DELAYED AND PULSED RELEASE OF BIOLOGICALLY ACTIVE SUBSTANCES

[75] Inventors: Margaret A. Wheatley, Arlington; Robert S. Langer, Somerville; Herman N. Eisen, Waban, all of Mass.

[73] Assignee: Massachusetts Institute of Technology, Cambridge, Mass.

[21] Appl. No.: 161,198

[22] Filed: Feb. 23, 1988

Related U.S. Application Data

[63] Continuation of Ser. No. 727,802, Apr. 26, 1985, abandoned.

[51] Int. Cl.[4] .............................................. A61K 37/22
[52] U.S. Cl. .................................... 424/450; 514/963
[58] Field of Search ................................ 424/417, 450

[56] References Cited

U.S. PATENT DOCUMENTS

| | | | |
|---|---|---|---|
| 4,145,410 | 3/1979 | Sears | 424/450 |
| 4,217,344 | 8/1980 | Vanlerberghe et al. | 424/60 |
| 4,314,557 | 2/1982 | Chandrasekaran | 424/449 |
| 4,352,883 | 10/1982 | Lim | 435/178 |
| 4,708,861 | 11/1987 | Popescu et al. | 424/1.1 |
| 4,731,210 | 3/1988 | Weder et al. | 264/4.3 |
| 4,761,288 | 8/1988 | Mezei | 424/450 |

OTHER PUBLICATIONS

"Liposomes", Gregoriadis, Drug Carriers in Biology and Medicine, Ch.14, 287–341 (1979, Academic Press, NY).

"Lysosomal Localization of B-Fructofuranosidase–Containing Liposomes Injected Into Rats", Biochem. J., 129, 123–133 (1972), Gregoriadis et al.

Francis Szoka et al., "Procedure for Preparation of Liposomes w/Large Internal Aqueous Space and High Capture by Reverse-Phase Evaporation", Proc. Natl. Acad. Sci., USA, 75(9), 4194–4198 (1978).

"A Simple Method for the Preparation of Homogeneous Phospholipid Vesicles", Biochemistry, 16(12), 2806–2810 (1977), Barenholz et al.

"Preparation of Homogeneous Single-Walled Phosphatidylcholine Vesicles", Methods in Enzymol., 32, 485–489 (1974), Huang et al.

"The Preparation of Large Single Bilayer Liposomes by a Fast and Controlled Dialysis", Biochem. Biophys. Acta, 512, 147–155 (1978), Milsmann et al.

"Large Volume Liposomes by an Ether Vaporization Method", D. Deamer et al., Biochem. Biophys. Acta, 443, 629–634 (1976).

"Drug Entrapment in Liposomes", Gregoriadis, Febs Letters, 36(3), 292–296 (1973).

(List continued on next page.)

Primary Examiner—Douglas W. Robinson
Assistant Examiner—Raymond J. Henley, III
Attorney, Agent, or Firm—Kilpatrick & Cody

[57] ABSTRACT

A system for controlled release both in vivo and in vitro of entrapped substances, either at a constant rate over a period of time or in discrete pulses, is disclosed. Biologically active substances, such as drugs, hormones, enzymes, genetic material, antigens including viruses, vaccines, or inorganic material, such as dyes and nutrients, are entrapped in liposomes which are protected from the biological environment by encapsulation within semi-permeable microcapsules. Release of the entrapped substance into the surrounding environment is governed by the permeability of both the liposome and microcapsule walls to the substance. Permeability of the liposome is engineered by modifying the composition and method for making the liposomes, thereby producing liposomes which are sensitive to a specific stimuli such as temperature, pH, or light; or by including a phospholipase within some or all of the liposomes or the microcapsule; or by destabilizing the liposomes to break down over a period of time; or by any combination of these features.

24 Claims, 3 Drawing Sheets

OTHER PUBLICATIONS

"pH–Triggering of Phosphatidylcholine Membrane Properties Via Complexation w/Synthetic Poly(Carboxylic Acid)s", Seki et al., Proc. of ACS Div. Polymer Material Mtg, Philadelphia, PA, ACS, 51, 216–219 (1984).

"Photoresponsive Artificial Membrane, Regulation of Membrane Permeability of Liposomal Membrane by Photoreversible Cis–Trans Isomerization of Azobenzenes", Kano et al., *Photo Chem. Photobiol.*, 34, 323–329 (1981).

"Photoresponsive Membranes, Regulation of Membrane Properties by Photoreversible Cis–Trans Isomerization of Azobenzenes", Kano et al., *Chem. Lett*, 421–424 (1980).

"pH Sensitization of Phospholipid Vesicles via Complexation W/Synthetic Poly(Carboxylic Acid)s", Tirrell et al., *Annals of NY Acad. of Sci.*, vol. 446, 237–248 (Jun. 21, 1985).

"Immobilization of Whole Bacterial Cells to Aid in the Saccharification of Cellulosic Carbohydrate Substrates", Wheatley et al., *Adv. Biotech.*, pp. 47–54 (1980).

"Possible Use of Agarose Gels as Encapsulating Media for Transplantation of Islets of Langerhans", Howell et al., *Proc. Physiol. Soc.*, 20p–21p (Nov. 1981).

"Influence of Liposomal Drug Entrapment on Percutaneous Absorption", Ganesan et al., *Int. J. of Pharmaceutics.*, 20, 139–154 (1984).

"Sustained Delivery of Polypeptide Hormones Using the Liposome–Collagen Gel Matrix", Weiner et al., *Fed. of Am. Soc. of Expt. Biol.*, 69th Annual Mtg., Anaheim, CA, *Fed. Abst.* 44(4), 4848 (1985).

Papahadjopoulos et al., *Biochem. Biophys. Acta*, 135, 639–652 (1967).

Jackson et al., *Biochemistry*, 21, 4576–4582 (1982).

- WATER SOLUBLE MOLECULES
| LIPID SOLUBLE MOLECULES
Y WATER SOLUBLE MOLECULES WITH HYDROPHOBIC MOIETY PENETRATING LIPID PHASE

SYSTEM FOR DELAYED AND PULSED RELEASE OF BIOLOGICALLY ACTIVE SUBSTANCES

The present application is a continuation to U.S. Ser. No. 727,802 filed Apr. 26, 1985 by Margaret A. Wheatley, Robert S. Langer and Herman N. Eisen entitled "System for Delayed and Pulsed Release of Biologically Active Substances", now abandoned.

The present invention is a method and system for controlled in vitro or in vivo release of substances, where release may be continuous over a period of time or in discrete pulses, wherein the substances are entrapped within specifically formulated and prepared liposomes which are protected from the biological environment by encapsulation within microcapsules.

BACKGROUND OF THE INVENTION

Liposomes are highly advanced assemblages consisting of concentric closed membranes formed by water-insoluble polar lipids, particularly phospholipids. Other substances, such as cholesterol, may also be included in the membrane. Stability, rigidity, and permeability of the liposomes are altered by changes in the phospholipid composition. Membrane fluidity is generally controlled by the composition of the fatty acyl chains of the lipid molecules. The fatty acyl chains can exist in an ordered, rigid state or in a relatively disordered fluid state. Factors affecting rigidity include chain length and degree of saturation of the fatty acyl chains and temperature. Larger chains interact more strongly with each other so fluidity is greater with shorter chains. Saturated chains are more flexible than unsaturated chains. Transition of the membrane from the rigid to the fluid state occurs as the temperature is raised above the "melting temperature". The melting temperature is a function of the length and degree of unsaturation of the fatty acyl chain.

In addition to temperature and phospholipid composition, inclusion of a sterol, such as cholesterol, or a charged amphiphile can alter the stability, rigidity and permeability of the liposome by altering the charge on the surface of the liposome and increasing the distance between the lipid bilayers. Proteins and carbohydrates may be incorporated into the liposomes to further modify their properties.

Liposomes are classically prepared by dissolving an appropriate concentration of phospholipid in an organic solvent, evaporating the solvent, and subsequently disrupting the dry lipid layer with excess water or buffer. Substances can be entrapped within the liposomes during formation. "Entrapment" is defined as either the incorporation of a lipophilic substance into the lipid framework of the bilayer or the passive encapsulation of a water-soluble substance in the aqueous compartments. These substances include proteins such as enzymes, hormones, and globulins, polyamino acids, nucleic acids, drugs, vitamins, and virus. An excellent review of liposomes and substances which have been incorporated into liposomes is "Liposomes" by Gregory Gregoriadis found in *Drug Carriers in Biology and Medicine,* Chapter 14, 287-341, G. Gregoriadis ed. (Academic Press, N.Y., 1979).

The first studies of in vivo injection of liposomes investigated introduction of enzymes into cells via liposomes. Other studies followed on the transport of various substances into otherwise inaccessible cellular regions, both in vivo and in vitro. In general, the fate of liposomes in vivo is dependent on their size, charge, lipid composition and other physical characteristics. Injected intravenously, larger or negatively charged liposomes are cleared more rapidly than smaller or neutral or positively charged ones. Liver and spleen tissues are primarily responsible for removal of liposomes from the blood and the peritoneal cavity. Following local injection, large liposomes are retained and disintigrated at the site of injection. Small, subcutaneously injected liposomes enter the circulation.

A study by Gregoriadis and Ryman entitled "Lysosomal Localization of Beta-Fructofuranosidase Containing Liposomes Injected Into Rats" in *Biochem J.* 129, 123-133 (1972) reported in vivo distribution of radioactive beta-fructofuranosidase-containing liposomes over time. Activity was found to decline to 50% of the injected dose within one hour. With six hours much of the activity was recovered in the liver and spleen.

In general, the extent of retention in vivo of substances by liposomes is dependent on the physical characteristics of the substance such as molecular weight or hydrophobic bonding, composition and integrity of the liposomes, and the presence of disruptive blood components. For example, addition of 10 mole % or more of cholesterol into the lipid bilayer may decrease release of an entrapped substance while interaction of some blood components with the liposomes may dramatically increase the rate of release.

Unfortunately, there are a number of disadvantages to using liposomes as an in vivo drug carrier. For example, liposomes are known to act as powerful immunological adjuncts to entrapped antigens and caution must be exercised when enzymes or other proteins of xenogeneic origin are entrapped in the liposomes. The rate of diffusion of the drug is difficult to control. This is a function of the inherent instability of the liposomes as well as the presence of specific blood components which accelerate the diffusion of certain drugs through liposomal bilayers. By their nature, some substances are poorly entrapped in liposomes and diffuse rapidly in circulation. Release of the entrapped substance in "pulses" or at a specified time or in response to a particular stimuli has not yet been possible. Still another problem has been the difficulty of targeting any cells or organ other than the liver or spleen.

It is therefore an object of the present invention to provide a method and system wherein substances are entrapped in liposomes for subsequent in vivo or in vitro release and where the time and duration of release of the entrapped substance are controlled by manipulation of the liposomes.

It is a further object of the present invention to provide such a system wherein the liposomes are protected from destructive forces in their biological environment, such as shearing forces in blood and tissues or the enzymatic action of lipases or other enzymes in tissue or blood, or phagocytosis by macrophages or polymorphonuclear leukocytes.

It is yet another object of the invention to provide a system wherein multiple entrapped substances can be combined and/or sequentially released in response to a specific stimuli or after a predetermined time.

SUMMARY OF THE INVENTION

A system and method for controlled in vivo or in vitro release of substances comprising entrapping the substances in liposomes and encapsulating the liposomes within microcapsules. The substances may include biologically active substances such as proteins (including enzymes, hormones, or immunoglobulins), polyamino acids, viruses, nucleic acids, drugs, vitamins, or other small molecules, including inorganic materials such as dyes, nutrients, or pesticides. These substances may be water soluble and contained completely within the aqueous spaces of the liposomes, they may contain lipophilic portions which are interspersed between the lipid molecules, or they may be bound to an inert carrier which prevents the substance from diffusing out of the liposomes. Additional or other substances may be bound to the interior of the microcapsule, solubilized within the aqueous space of the microcapsule wall or bound to an inert carrier which is retained within the microcapsule.

The liposomes are specifically formulated and manufactured to have particular physical characteristics such as size, permeability, and stability. They may be further designed to be sensitive to specific stimuli such as pH, temperature and light or to be susceptible to degradation by a particular encapsulated enzyme such as a phospholipase. The encapsulated liposomes may also be sonicated under various conditions that will cause disruption of different proportions of liposomes. Disruption of the liposomes may also be by exposure to an agent such as a detergent, high ionic strength solution, or bivalent metal. The liposomes may be co-encapsulated with additional biologically active substances which are not entrapped within the liposomes. This provides an initial release of the additional substance prior to the release of the substance within the liposomes. By manipulation of the liposome composition and method of manufacture, the release of the entrapped substance into the surrounding medium can be controlled. This release may be steady over a period of time or occur at discrete times in response to the specific stimuli.

The liposomes are encapsulated in microcapsules, for example, formed with a core of alginate crosslinked with calcium ions selectively coated with a polycationic skin made using polymers such as poly-L-lysine and polyvinyl amine. The permeability of the microcapsule wall further acts to control the rate of diffusion of the entrapped substance into the surrounding medium. The microcapsule also provides a means to minimize the potential for an immune response directed against the liposomes.

The only restriction on the type of capsule is that the method of manufacture does not cause the liposome to be destroyed during encapsulation.

In this embodiment, liposomes are prepared from phosphatidyl choline, phospatidyl glycerol, and cholesterol in a molar ratio of 9:1:8 using reverse phase evaporation and then encapsulated in microcapsules of the preferred composition. The substance is entrapped during formation of the liposomes.

In an example of the present invention, encapsulated liposomes were used in a two-pulse delivery system for myoglobin using selective disruption of a fraction of the liposomes on administration followed by a second release after 600 hours at the natural breakdown point of the undisturbed liposome fraction remaining in the microcapsule.

There are several advantages to the use of encapsulated liposomes: the inherent instability of the liposomes is used to expand and enhance the times and rates possible for release of the entrapped substance so that it is no longer a disadvantage; the encapsulated liposomes are too large to be extensively scavenged by the RES system but can still be subcutaneously or intraperitoneally injected; the entrapped active substance can be released according to a pulsed regime or at a constant rate over time; additional or other substances can be enclosed within the microcapsule; and the system can be designed to use specific external stimuli to trigger release.

DETAILED DESCRIPTION OF THE INVENTION

Figure 1:
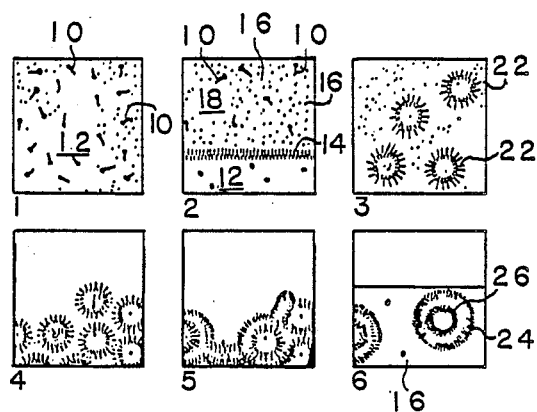
FIG. 1 is a diagram of the proposed mechanism of formation of lipid vesicles or liposomes by the reverse phase evaporation method.

The method for controlled release of substances comprises: entrapping at least one substance within liposomes wherein the composition and method of preparation are selected to produce liposomes with a predetermined rigidity, stability and permeability, wherein the substance is contained within the aqueous compartment, either in solution, bound to other molecules, or bound to another solid medium, or the substance is incorporated into the membrane of the liposome; encapsulating the liposomes in microcapsules, wherein the composition and method of preparation of the microcapsules are selected to produce microcapsules of a desired diameter, permeability, non-immunogenicity, and compatibility with the liposomes, and wherein other biologically active or additional substances may be encapsulated within the microcapsules, either in solution, bound to the microcapsule wall, or bound to another medium such as an agarose bead; and locating the encapsulated liposomes at the desired release site.

The liposomes are formed primarily of a mixture of phospholipids. Cholesterol may be added to decrease membrane thickness, increase fluidity, and enhance solute entrapment. Charged phospholipids increase the volume of aqueous spaces within the liposomes and delay diffusion of entrapped ions of homologous charge. A number of possible lipid compositions is summarized on p. 293–306 of "Liposomes" by Gregory Gregoriadis. The lipid vesicles should have the following desirable properties: (i) the ability to entrap a large percentage of the aqueous material, even large macromolecular assemblies; (ii) a high aqueous space-to-lipid ratio; and (iii) a widely variable chemistry of the lipid components.

The liposomes may be prepared by any of a number of techniques known to those skilled in the art. The preferred method is by reverse-phase evaporation, described in "Procedure for Preparation of Liposomes with large internal aqueous space and high capture by reverse-phase evaporation" by Szoka and Papahadjopoulos in *Proc. Natl. Acad. Sci. USA*, 75(9), 4194–4198

(1978). Using this method, large unilamellar and oligolamellar vesicles are formed when an aqueous buffer is introduced into a mixture of phospholipid and organic solvent and the organic solvent is subsequently removed by evaporation under reduced pressure.

In the preparation of reverse-phase evaporation vesicles (REV), several phospholipids, either pure or mixed with other lipids such as cholesterol, long-chain alcohols, etc., are used with similar results. As described by Szoka et al., the lipid mixture is added to a 50-ml round-bottom flask and the solvent removed under reduced pressure by a rotary evaporator. The system is then purged with nitrogen and the lipids redissolved in the organic phase to form the reverse phase vesicles. Useful solvents include diethyl ether, isopropyl ether, halothane and trifluorotrichloroethane. When the lipid has low solubility in ether, chloroform or methanol can be added to increase its solubility. At this point, the aqueous phase is added under nitrogen and the resulting two-phase system sonicated briefly (2–5 min. at 0–5° C. for most lipids) until the mixture becomes either a clear one-phase dispersion or a homogeneous opalescent dispersion that does not separate for at least 30 min. after sonication. The degree of opalescence of the preparation at this point depends upon the solvent, phospholipid, and amount of aqueous phase in the preparation. The mixture is then placed on a rotary evaporator with a long extension neck, and the organic solvent removed under reduced pressure at 20–25° C., rotating at approximately 200 rpm.

The system froths during evaporation of the solvent. As the majority of the solvent is removed, the material first forms a viscous gel and subsequently, within 5–10 min., becomes an aqueous suspension. At this point, excess water or buffer can be added and the suspension evaporated for an additional 15 min. at 20° C. to remove traces of solvent. When lipid mixtures lacking cholesterol are used at low concentrations of <7.5 umol of lipid per ml of aqueous phase, the gel phase may not be apparent since the system rapidly reverts to a lipid-in-water suspension. To remove non-encapsulated material and residual organic solvent, the preparation is then either dialyzed, passed through a Sepharose 4B ™ (Pharmacia Fine Chemicals, Piscataway, NJ) column, or centrifuged (100,000×g for 30 min.).

The vesicles may be filtered or passed through a molecular seive column to give a more uniform vesicle size. For example, filtration through a 200 nm Unipore filter yields a vesicle size of 120–300 nm. A large number of variables may be responsible for determining the final product in terms of vesicle size. These include the type of phospholipid and its solubility in the organic solvent, the interfacial tension between aqueous buffer and organic solvent, and the relative amounts of water phase, organic solvent, and phospholipids.

The entrapment of a particular molecule within the vesicles is dependent on several variables, including the ionic strength of the buffer. As the ionic strength is increased, there is a decrease in both the percent encapsulation and the volume of encapsulated aqueous space per mole of phospholipid. Varying lipid concentration can increase the amount of capture up to about 45% in 0.15 M NaCl. The percentage of molecules encapsulated decreases with decreasing total lipid but the ratio of aqueous volume within the vesicle/mole of phospholipid increases. Different lipid compositions encapsulate different amounts of liquid. The addition of cholesterol significantly increases the volume of encapsulated liquid. Reverse-phase evaporation vesicles (REV) tend to capture a larger volume of aqueous space than do multilamella (MLV) and sonicated unilamella vesicles (SUV).

The proposed formation of lipid vesicles with simultaneous entrapment of suspended molecules is diagrammed in FIG. 1. In panel 1, lipids 10 are dissolved in the appropriate solvent 12. In panel 2, lipids 10 form a bilayer membrane 14 structure as the compound 16 to be entrapped is added. In panel 3, the initial sonication of the buffered aqueous phase 18 in the organic solvent 12 in the presence of amphiphatic phospholipid molecules produces small water droplets 20 stabilized by a phospholipid monolayer 22. In panel 4, the droplets or "inverted micelles" 20 are collapsed to form a viscous gel-like material 23 when the organic phase 12 is removed by evaporation. In panel 5, the gelled material 23 collapses. Very little additional material 16 is entrapped by the vesicles 20 at this point. In panel 6, some of the inverted micelles 20 disintigrate, releasing their entrapped material 16. The excess lipid contributes to a complete bilayer 24 around the remaining micelles 20, resulting in the formation of vesicles 26.

Other methods for the entrapment of molecules by formation of liposomes may be used in the present invention. A method for the preparation of large unilamella vesicles (LUVs) is described in "A Simple Method for the Preparation of Homogeneous Phospholipid Vesicles" by Barenholz et al. in *Biochemistry*, 16(12), 2806–2810 (1977). This method involves differential high-speed ultracentrifugation of sonicated aqueous lipid suspensions.

A method for "Preparation of Homogeneous, Single-Walled Phosphatidyl Choline Vesicles" by Huang and Thompson in *Methods in Enzymol.* 32, p. 485–489 (1974) yields spherical, homogeneous vesicles each comprised of a single continuous lipid bilayer. The method consists of suspending the lipid in an aqueous salt solution, sonicating the suspension at 2° C. under an inert gas to prevent oxidation, centrifuging, concentrating by ultrafiltration, and sizing by column chromatography. Sonication at higher temperatures or in air causes degradation of the phospholipid by oxidation of the unsaturated acetyl chains or hydrolysis of the ester bonds. The resulting instability of the liposomes can be manipulated to advantage in the present invention.

"The Preparation of Large Single Bilayer Liposomes by A Fast and Controlled Dialysis" by Milsmann et al. in *Biochem. Biophys. Acta*, 512, 147–155 (1978) discloses another method for preparing single bilayer phospholipid vesicles. This method is based on a fast and controlled dialysis of sodium cholate from phosphatidyl choline/cholate mixed micelles.

Yet another method for preparation of liposomes is taught by "Large Volume Liposomes by an Ether Vaporization Method" by Deamer and Bangham in *Biochem. Biophys. Acta*, 443, 629–634 (1976). This method forms unilamellar liposomes by injecting ether solutions of various lipids into a warm aqueous solution.

Still another method for preparation of liposomes with entrapped molecules is described by Gregoriadis in *FEBS Letters*, 36(3), 292–296 (1973). This method is similar to the preferred method, consisting of dissolving the lipids in chloroform and evaporating the solvent under vacuum along with aqueous solution of the substances to be entrapped.

The liposomes may be designed and prepared to respond to a specific stimulus, or combination of stimuli, as well as to have a particular stability, rigidity, and permeability. All liposomes are inherently unstable due to interactions between the particular lipids they are comprised of and their environment. However, other stimuli such as pH, temperature, or light can be used to trigger release of entrapped material at a more specific time.

"pH-triggering of phosphatidyl choline membrane properties via complexation with synthetic poly(carboxylic acid)s" by Seki et al in "Polym. Materials Sciences and Eng." Proc. of ACS. Div. of Polym. Materials Meeting in Philadelphia, Pa. *ACS,* 51, 216–219 (1984) describes the use of a synthetic poly(carboxylic acid), poly(alphaethylacrylic acid) PEAA to effect a pH-dependent release of the contents of vesicles formed from egg yolk phosphatidyl choline. Phosphatidyl choline vesicles are unaffected by PEAA at high pH but are rendered unstable at pH 7 or below. Since the pH of lysosomes is approximately 4.6, liposomes which are intact when they circulate in the bloodstream at physiological pH may be stimulated to release their contents when they are taken up by the lysosome-containing cells, usually by endocytosis.

Liposomes which undergo dramatic increases in permeability when irradiated with light are known. Two photosensitive phospholipids, 1,2-diretinoyl-Sn-glycero-3-phosphocholine and 1-palmitoyl,2-retinoyl-Sn-glycero-3-phosphocholine, are described by Pidgeon and Hunt in "Light Sensitive Liposomes" in *Photochem and Photobiol.* 37, 491–494 (1983). The permeability of liposomes formed from either or both of these phospholipids is directly proportional to temperature. Upon exposure to 30 to 120 seconds of 360 nm light, the permeability of the liposomes increases dramatically, from approximately 20% to almost 90%.

Another photosensitive system is described by Kano et al. in *Photochem. Photobiol.* 34, 323–325 (1981) and *Chem. Lett.* 421–424 (1981). Kano et al showed that incorporation of light isomerizable azobenzene lipids into liposome membranes produces vesicles with increased membrane permeability upon exposure to light.

The sensitivity of liposomes to temperature is also well known. Specific lipid compositions may be formulated so that their transition temperature is above the temperature at which the liposomes are to store the biologically active substances yet low enough to allow for release when the temperature is raised slightly. In vivo, this may be done as easily as subcutaneously injecting encapsulated liposomes, then applying a heating pad to stimulate release.

The liposomes may also be destabilized using phospholipase enzymes. These may be entrapped within the liposomes or packaged within the surrounding microcapsule. To prevent diffusion or release of the enzyme from the liposome or microcapsule, the enzyme molecular weight may be increased by a number of methods, causing the enzyme to be trapped inside the capsule. For example, the phospholipase may be linked chemically or ionically to solid media such as Sephadex TM, CM-Sephadex TM or DEAE-Sephadex TM (Pharmacia Fine Chemicals, Piscataway, NJ) or cross linked between enzyme molecules with bifunctional reagents such as gluteraldehyde, possibly in the presence of substrate to protect the active site. Also, the enzyme could be covalently linked to a soluble polymer such as poly-L-lysine. The phospholipase is selected for ability to cleave one or more of the phospholipids making up the liposome, and non-toxicity to the organism or surrounding cells if for in vivo use.

For in vitro systems, other agents may be added to the solution to stimulate release of the entrapped material. For example, detergents such as Triton X100 or high salt solutions can diffuse into the microcapsule with subsequent disruption of the liposomes. Non-ionic detergents such as octyl glucoside can be used, and have the advantage of being less damaging to proteins as compared to ionic detergents, as shown by M.L. Jackson et al, *Biochem.* 21, 4576–4582 (1982). Bivalent metals have also been shown by D. Papahadjopoulos and J.C. Watkins in *Biochem. Biophys. Acta.* 135, 639–652 (1967) to increase the permeability of liposomal bilayers.

Other stimuli and methods for preparing liposomes which are responsive to these stimuli and characterized by a particular rigidity, permeability, and stability are known to those skilled in the art. Essentially, any method for preparing liposomes which become unstable after a predetermined period of time or whose permeability can be significantly altered by manipulation of the immediate environment, either in vivo or in vitro, may be used in the present invention.

A variety of substances can be entrapped within the liposomes. Examples are proteins (such as enzymes, hormones, and globulins), polyamino acids, virus particles, nucleic acids, vitamins, and other small molecules, including inorganic compounds such as drugs, dyes, pesticides, and nutrients.

Figure 2:
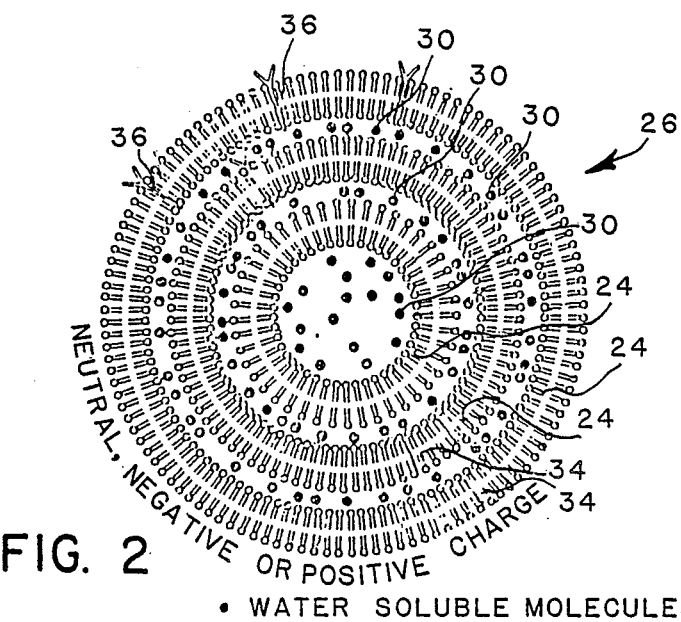
FIG. 2 is a diagrammatic representation of a liposome in which three bilayers of polar phospholipids alternate with aqueous compartments.

As shown in FIG. 2, any water soluble 30 or suspendable molecule can be encapsulated in the aqueous portion 32 of a liposome 26. Lipid soluble molecules 34 can be incorporated into the lipid bilayers 24. Hydrophobic ends 36 of water soluble molecules can also be inserted into the lipid layers 24.

In the method of the present invention, the liposomes are encapsulated within microcapsules consisting of any non-toxic polymer or mixture of polymers which can be formed into capsules using a method which does not harm the liposomes and which results in capsules of the desired diameter, rigidity, permeability, and stability.

The preferred method is taught by U.S. Pat. No. 4,352,883 to Lim. Using this method, 500 micron diameter (sized by gel filtration) capsules with a permeability of approximately 6,000 to 40,000 m.w. are formed with a core of alginate crosslinked with calcium ions selectively coated with a polycationic skin using polymers such as poly-L-lysine and poly-vinyl amine.

The process is as follows: the liposomes, containing the entrapped substances, are encapsulated in a physiologically compatible medium containing a water soluble substance that can be made insoluble (gelled). The medium is then formed into droplets around the liposomes and gelled by changing temperature, pH or ionic strength. The gelled droplets are then treated to produce membranes of a controlled permeability about the gelled droplets. The presently preferred material for forming the temporary capsules is polysaccharide gums, either natural or synthetic, of the type which can be gelled to form a shape retaining mass by exposure to a different pH or multivalent cations such as Ca++ and ionically crosslinked by polymers containing reactive groups such as amine or imine groups which can react with acidic polysaccharide constituents. Gelatin or agar may be used in place of the polysaccharide gums.

Figure 3:
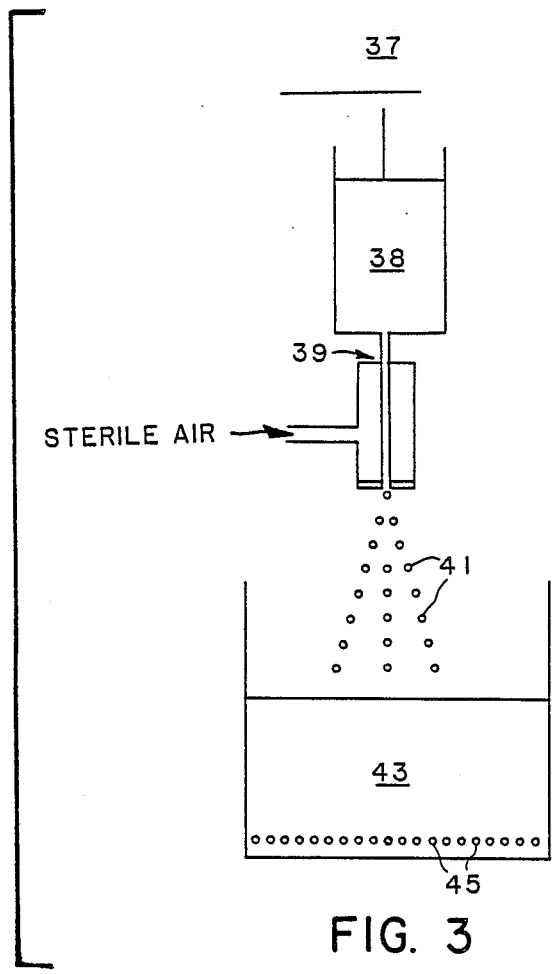
FIG. 3 is a diagram of primary capsule formation encapsulating liposomes.

As shown in FIG. 3, the preferred method of formation of the droplets is to use a syringe pump 37 to force the sodium alginate-liposome suspension 38 through a capillary tube or 22 gauge needle 39 around which flows a coaxial stream of air. Droplets 41 ejected from the tip of the needle 39 immediately contact a 1.5% CaCl₂ solution 43 and gel as sphere-shaped bodies 45.

The preferred method of forming a permanent semipermeable membrane about the temporary capsules is to "crosslink" surface layers of the gelled alginate using a dilute solution of polyamino acids such as poly-L-lysine and poly-vinyl amine. Generally, the lower the molecular weight of the polymer, the greater the penetration into the surface of the temporary capsule and the less permeable the resulting membrane. Ionic crosslinks are produced as a consequence of salt formation between the acid reactive groups of the crosslinking polymer and the acid groups of the polysaccharide gum. Within limits, permeability can be controlled by setting the molecular weight of the crosslinking polymer, its concentration, and the duration of reaction.

The in vivo life of the capsules is a function of the cross-linking polymer. For exaple, proteins or polypeptide crosslinkers, such as polylysine, are enzymatically attacked in vivo. Crosslinkers not readily digestible in mammalian bodies, such as polyethyleneimine, produce longer lasting membranes.

It is possible to improve mass transfer within the capsule after formation of the permanent membrane by re-establishing the conditions under which the material forming the temporary capsule is liquid, for example, by removing the multivalent cation by ion exchange in phosphate buffered saline containing citrate.

Other methods and materials for encapsulating liposomes include the method of Wheatley and Phillips in *Adv. in Biotechnol.* II, 47–54 (1980) which uses entrapment in polyacrylamide gels. The gels are polymerized by free radical polymerization using potassium persulfate as the initiator and beta-dimethylaminopropionitrile as the promotor. In this case the reaction results in a sheet of polymer which may be cut into fragments after the polymerization reaction is complete.

Thermal gelation of agarose gels, such as the method of Howel et al. in *Proc. Physiol. Soc.*, 20p—21p (November 1981) is another possible method. The agarose, Seaprep 15/45 TM (FMC Corporation, Marine Colloids Division, Me.), can be loaded at 22° C. with the gels in their sol form. Cooling to 15° C. allows the gel to pass through the sole-gel transition and the agarose remains intact up to temperatures of 45° C. before it melts.

In general, the requirements for the method and materials for encapsulation are as follows:

The method must not destroy the integrity of the liposomes during encapsulation.

The capsule must retain the liposomes.

The capsule matrix must allow for diffusion of the drug out of the matrix after its release from the lipsome.

All materials for in vivo use must be non-toxic to the body.

There must be no chemical interaction between the components of the matrix and both the liposomes and the biologically active substance.

Figure 4:
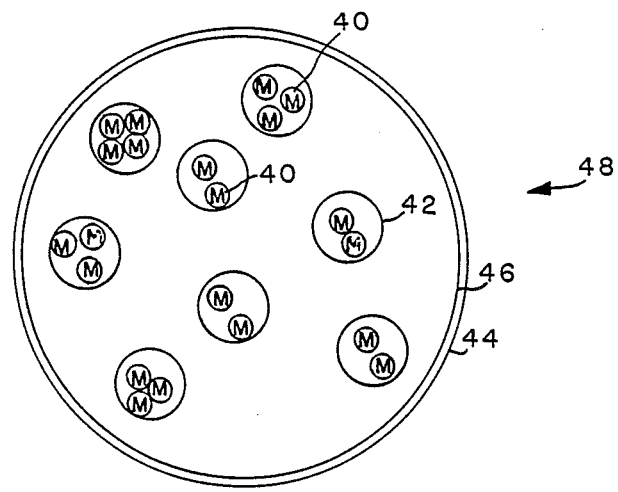
FIG. 4 is a diagrammatic representation of liposomes encapsulated in a microcapsule.

In one example of the present invention, shown in FIG. 4, myoglobin 40 containing-liposomes 42, prepared by reverse phase evaporation using the method of Szoka et al, *Proc. Natl. Acad. Sci. USA*, 75(9), 4194–4198 (1978) and comprising phosphatidyl choline, phosphatidyl glycerol, and cholesterol in a molar ratio of 9:1:8, were encapsulated in 500 micron diameter capsules 44, prepared with a core 46 of calcium ion-crosslinked alginate selectively coated with poly-L-lysine and poly-vinylamine and having a permeability of 6,000 to 40,000 mw.

Figure 5:
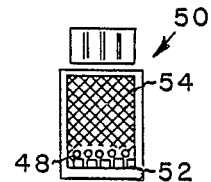
FIG. 5 is a vial containing microencapsulated liposomes used in an experiment to determine the in vitro release data graphed in FIG. 6.
Figure 7:
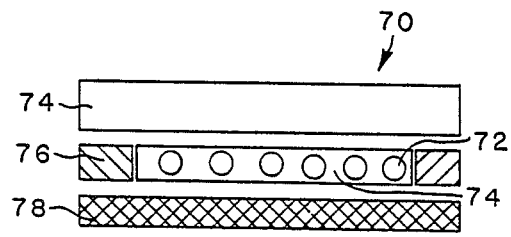

One ml. equivalents of encapsulated liposomes 48 were placed in vials 50, shown in FIG. 5. A 105 micron polypropylene mesh tube 54, sealed at the base with a wax plug 52, was used to retain the encapsulated liposomes 48. The vials 50 were then filled with 10 ml. of physiological saline and placed on a shaker. The temperature was maintained at 37° C. The physiological saline in the vials 50 was changed frequently to mimic the infinite sink conditions of the body.

Figure 6:
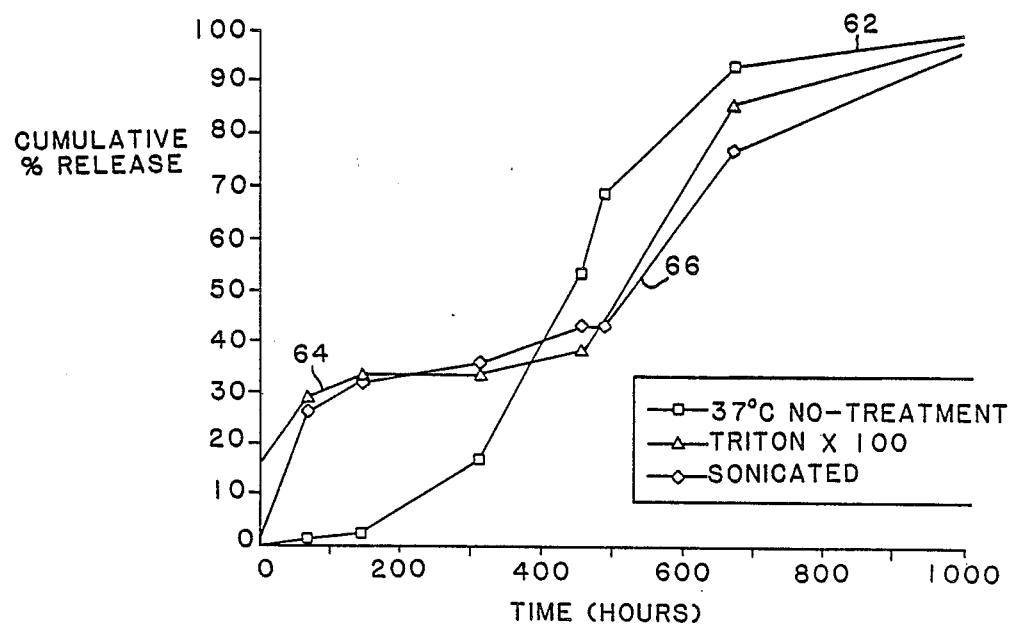
FIG. 6 is a graph of the release of myoglobin from encapsulated liposomes as a function of time.

Release of myoglobin 40 under various conditions was determined over time by absorbance at 410 nm. The results are graphed in FIG. 6. The experiment was conducted over a 1200 hour period. The untreated encapsulated liposomes 62 showed little release of entrapped myoglobin for the first 200 hours and then released approximately 90% over the next 500 hours. Encapsulated liposomes treated with Triton X100 64 displayed an initial release of approximately 30% at 100 hours, and a second burst of another 50% after 500 to 600 hours. Treatment involved brief contact with 10 ml of 0.1% Triton X100 in physiological saline, pH 7.4. After 5 minutes contact time the encapsulated liposomes were transferred to 10 mls of regular physiological saline and the experiment was continued in the normal manner. Sonicated liposomes 66 also showed an initial release of approximately 30% after 100 hours with a subsequent release of an additional 45% after another 500 to 600 hours. Sonication involved subjecting the encapsulated liposomes contained within the polypropylene tube in a vial filled with 10 ml of physiological saline, to a 5 minute burst of sonic energy. This was achieved by immersing the vial in cold (4° C.) water in a Laboratory Supplies Sonic bath G112SPIT. With the "untreated" 62, Triton X100 64, and sonicated 66 liposomes, almost 100% of the myoglobin had been released into the surrounding medium by 1000 hours. With the treated capsules, increasing treatment time led to greater release of entrapped material at the first pulse.

The results show that by varying the conditions to which the encapsulated liposomes are exposed, the entrapped material can be released immediately, slowly over a period of time, or in discrete pulses.

The present invention may be embodied in other specific forms without departing from the spirit and scope thereof. These and other modifications of the invention will occur to those skilled in the art. Such other embodiments and modifications are intended to fall within the scope of the appended claims.

We claim:

1. A microencapsulated system for controlled release of entrapped biologically active substances prepared by the process comprising:
   entrapping a first substance within liposomes, wherein the liposomes have a predetermined rigidity, permeability, stability, and sensitivity to specific stimuli,
   encapsulating the liposomes within microcapsules permeable to solutions and the substance to be released but impermeable to scavenging components of the reticuloendothelial system, having a predetermined diameter, rigidity, stability, and being non toxic to the encapsulated liposomes and host if implanted, wherein the substance in the liposomes is released by exposure of the encapsulated liposomes to a specific stimulus selected from the group consisting of pH, sonication, temperature, high ionic strength solutions, bivalent metals, detergents, phospholipases, and light.

2. The microencapsulated system of claim 1 further comprising entrapping a phospholipase with the active substance within said liposome.

3. The microencapsulated system of claim 1 further comprising a phospholipase located in the space between the wall of said microcapsule and said liposomes.

4. The microencapsulated system of claim 3 wherein said phospholipase is bound to said microcapsule.

5. The microencapsulated system of claim 3 wherein said phospholipase molecules are crosslinked.

6. The microencapsulated system of claim 3 wherein said phospholipase is bound to a soluble polymer substrate and said microcapsules are impermeable to said polymer substrate.

7. The microencapsulated system of claim 1 further comprising encapsulating a second biologically active substance within said microcapsules in the space surrounding the liposomes.

8. The microencapsulated system of claim 1 wherein said first entrapped substance is selected from the group of biologically active materials consisting of proteins, nucleic acids, viruses, and inorganic compounds.

9. The microencapsulated system of claim 7 wherein said second encapsulated substance is selected from the group of biologically active materials consisting of proteins, nucleic acids, viruses, and inorganic compounds.

10. A method for making a microencapsulated system for controlled release of entrapped biologically active substances comprising:
providing a first biologically active substance,
entrapping the first substance within liposomes, wherein the liposomes have a predetermined rigidity, permeability, stability, and sensitivity to stimuli selected from the group consisting of pH, sonication, temperature, high ionic strength solutions, bivalent metals, detergents, phospholipases, and light, such that exposure to a stimulus effects release of the entrapped substance from the liposomes, and,
encapsulating the substance-containing liposomes within microcapsules, wherein the microcapsules are permeable to solutions and the substance to be released but impermeable to scavenging components of the reticuloendothelial system, have a predeterined diameter, rigidity, stability, and are non-toxic to the encapsulated liposomes and host if implanted.

11. The method of claim 10 further comprising stimulating the release of the entrapped substance from the encapsulated liposomes by exposing the encapsulated liposomes to the specific stimulus that the effects release of the substance from the liposomes.

12. The method of claim 11 wherein release of the entrapped substance from the encapculated liposomes is stimulated by sonicating the liposomes.

13. The method of claim 11, wherein release of the entrapped substance from the encapsulated lipsomes is stimulated by exposing the encapsulated lipsomes to a lipid bilayer-disrupting agent.

14. The method of claim 13 wherein said lipid bilayer-disrupting agent is selected from the group consisting of surface active detergents, high ionic strength solutions, and bivalent metals.

15. A method for controlled release of an entrapped biologically active substance comprising:
releasing by exposure to a specific stimuli a first biologically active substance entrapped within encapsulated liposomes having a predetermined rigidity, permeability, stability, and sensitivity to specific stimuli selected from the group consisting of pH, sonication, temperature, high ionic strength solutions, bivalent metals, detergents, phospholipases, and light, such that exposure to a stimulus effects release of the entrapped substance from the liposomes, wherein the permeability of the liposomes has been disrupted after encapsulation within microcapsules that are permeable to solutions and the substance to be released but impermeable to scavenging components of the reticuloendothelial system, having a predetermined diameter, rigidity, stability, and non-toxicity to the encapsulated liposomes and host if implanted.

16. The method for controlled release of claim 15 wherein release from the encapsulated liposomes is stimulated by changing the pH of the medium surrounding the encapsulated liposomes.

17. The method for controlled release of claim 15 wherein release from the encapsulated liposomes is stimulated by exposure to light.

18. The method for controlled release of claim 15 wherein release from the encapsulated liposomes is stimulated by changing the temperature of the medium surrounding the encapsulated liposomes.

19. The method for controlled release of claim 15 further comprising encapsulating a phospholipase capable of degrading the liposomes.

20. The method for controlled release of claim 15 further comprising binding the phospholipase to the microcapsule wall to prevent diffusion of the phospholipase from the microcapsule.

21. The method for controlled release of claim 15 wherein the encapsulated liposomes are stimulated at discrete intervals of time to produce a pulsed release of the entrapped substance.

22. The method for controlled release of claim 15 further comprising encapsulating a second biologically active substance.

23. The method for controlled release of claim 22 wherein the second substance is encapsulated within the microcapsules and entrapped within the liposomes.

24. The method for controlled release of claim 15 further comprising encapsulating an additional first biologically active substance within the microcapsule exterior to the liposomes.

* * * * *